US009585976B2

(12) United States Patent
Powell et al.

(10) Patent No.: US 9,585,976 B2
(45) Date of Patent: Mar. 7, 2017

(54) AUTOMATED RADIOLABELLING METHOD

(75) Inventors: Nigel Anthony Powell, Buckinghamshire (GB); Brian Higley, Buckinghamshire (GB); Roger Paul Pettitt, Buckinghamshire (GB)

(73) Assignee: GE Healthcare Limited, Buckinghamshire (GB)

( * ) Notice: Subject to any disclaimer, the term of this patent is extended or adjusted under 35 U.S.C. 154(b) by 1292 days.

(21) Appl. No.: 12/089,726

(22) PCT Filed: Oct. 9, 2006

(86) PCT No.: PCT/GB2006/003758
§ 371 (c)(1),
(2), (4) Date: Apr. 10, 2008

(87) PCT Pub. No.: WO2007/042791
PCT Pub. Date: Apr. 19, 2007

(65) Prior Publication Data
US 2008/0226552 A1 Sep. 18, 2008

(30) Foreign Application Priority Data
Oct. 10, 2005 (GB) .................................. 0520529.9

(51) Int. Cl.
*A61K 51/00* (2006.01)
*A61M 36/14* (2006.01)
*A61K 51/04* (2006.01)

(52) U.S. Cl.
CPC ................................ *A61K 51/0448* (2013.01)

(58) Field of Classification Search
CPC .... A61K 49/00; A61K 51/0497; A61K 51/06; A61K 51/1282; A61K 51/1286; A61K 51/00; A61K 51/02; A61K 51/04; A61K 2123/00; A61K 2121/00; A61K 51/0448; C07F 13/00; C07F 13/005; C07F 7/2212; C07F 7/22; C07F 7/2216
USPC .......... 424/1.11, 1.49, 1.65, 1.69, 1.73, 1.81, 424/1.85, 1.89, 9.1; 206/223, 569, 570
See application file for complete search history.

(56) References Cited

U.S. PATENT DOCUMENTS

| 7,229,603 B2 * | 6/2007 | Kuperus et al. .............. 424/1.65 |
| 7,586,102 B2 * | 9/2009 | Mourtada et al. ...... 250/432 PD |
| 8,221,720 B2 * | 7/2012 | Luthra .................... C07B 59/00 424/1.11 |
| 2004/0028573 A1 * | 2/2004 | Schmitz et al. .............. 422/130 |

FOREIGN PATENT DOCUMENTS

| GB | 1505982 | 4/1978 |
| WO | 98/18499 | 5/1998 |
| WO | 02/051447 | 7/2002 |
| WO | WO 02/051447 | 7/2002 |
| WO | 2004/071571 | 8/2004 |
| WO | 2005/107819 | 11/2005 |
| WO | WO 2006/134035 | 12/2006 |

OTHER PUBLICATIONS

Plascjak et al (Appl. Radiat. Isot., 1997, vol. 48, No. 3, pp. 345-348).*
Baldwin et al, Nucl. Med. Biol., 1995, vol. 22, pp. 211-219.*
Luurtsema et al, Applied Radiation and Isotopes, 2001, vol. 55, No. 6, pp. 783-788.*
Zea-Ponce et al, J. Nucl. Med., 1995, vol. 36, No. 3, pp. 525-529.*
Yoshizumi et al (J. Nucl. Med., 2000, vol. 41, No. 7, pp. 1134-1138).*
Toyama et al (Annals of Nuclear Medicine, 1993, vol. 7, No. 1, pp. 29-38).*
Gill et al (Br. Hear. J., 1993, vol. 69, pp. 6-13).*
Schlake et al (Neurosurg. Rev., 1987, vol. 10, pp. 191-196).*
Elliott et al (Eur. J. Nucl. Med., 1982, vol. 7, pp. 58-61).*
Database WPI Week Oct. 2005 Derwent Publications Ltd., London, GB: AN 2005-086858 XP002438892 & KR 204 075 625 A (Korean Atomic energy Res Inst) Aug. 30, 2004.
GB0520529.9 Search report dated Feb. 28, 2006.
PCT/GB2006/003758 Int'l Search Report/Written Opinion dated Jul. 16, 2007.
Baldwin, R., et al., Nuclear Medicine & Biology, 1993, vol. 20, No. 5, p. 597-606.
Chaly, T., et al., Applied Radiation and Isotopes, 1990, vol. 41, No. 1, p. 29-34.
Chaly, T., et al., Applied Radiation and Isotopes, 1993, vol. 44, No. 5, p. 869-873.
Chaly, T., et al., Nuclear Medicine & Biology, 1996, vol. 23, No. 8, p. 999-1004.
Matsumoto, H., et al., Frontiers of the Medicine in the New Century—Imaging of the Brain Function—Nihon Medi-Physics Co., Ltd., May 31, 2001, vol. 2001-I, p. 46-54.
Neumeyer, J., et al., Journal of Medicinal Chemistry, 1991, vol. 34, No. 10, p. 3144-3146.
Neumeyer, J., et al., Journal of Medicinal Chemistry, 1994, vol. 37, No. 11, p. 1558-1561.
Zea-Ponce, Y., et al., Journal of Nuclear Medicine, 1995, vol. 36, No. 3, p. 525-529.
Patent Abstracts of Japan, 07-318695, Dec. 8, 1995, Takeda Chem Ind Ltd.
Patent Abstracts of Japan, 07-318694, Dec. 8, 1995, Seitai Kinou Kenkyusho:KK.

(Continued)

*Primary Examiner* — D L Jones
(74) *Attorney, Agent, or Firm* — Wood IP LLC

(57) ABSTRACT

The present invention provides an automated method for the preparation of $^{123}$I-labelled radiopharmaceutical compositions, together with disposable cassettes for use in the method. The use of an automated synthesizer apparatus in the preparation of $^{123}$I-labelled radiopharmaceuticals is also described. Also described is the use of cassettes of the present invention in the preparation of $^{123}$I-labelled radiopharmaceuticals.

15 Claims, No Drawings

(56) References Cited

OTHER PUBLICATIONS

Patent Abstracts of Japan, 08-026975, Jan. 30, 1996, Seitai Kinou Kenkyusho:KK.
Patent Abstracts of Japan, 2005-106658, Apr. 21, 2005, Natl Inst of Radiological Sciences.
Satyamurthy, et.al. Clinical Positron Imaging vol. 2, No. 5, 1999 pp. 233-251.
Oh, et.al. Nuclear Medicine and Biology vol. 31, 2004 pp. 803-809.
Shibuya, et.al. Faculty of Medical Sciences 2000 pp. 35-39.
Bolton, R., "Radiohalogen incorporation into organic systems", J Label Compd Radiopharm, 45:485-528 (2002).

* cited by examiner

SEQUENCE LISTING

```
<160> NUMBER OF SEQ ID NOS: 14

<210> SEQ ID NO 1
<211> LENGTH: 5
<212> TYPE: PRT
<213> ORGANISM: Artificial
<220> FEATURE:
<223> OTHER INFORMATION: synthetic peptide

<400> SEQUENCE: 1

Tyr Ile Gly Ser Arg
1               5

<210> SEQ ID NO 2
<211> LENGTH: 5
<212> TYPE: PRT
<213> ORGANISM: Artificial
<220> FEATURE:
<223> OTHER INFORMATION: synthetic peptide

<400> SEQUENCE: 2

Pro Asp Ser Gly Arg
1               5

<210> SEQ ID NO 3
<211> LENGTH: 5
<212> TYPE: PRT
<213> ORGANISM: Artificial
<220> FEATURE:
<223> OTHER INFORMATION: synthetic peptide

<400> SEQUENCE: 3

Ile Lys Val Ala Val
1               5

<210> SEQ ID NO 4
<211> LENGTH: 3
<212> TYPE: PRT
<213> ORGANISM: Artificial
```

```
<220> FEATURE:
<223> OTHER INFORMATION: synthetic peptide

<400> SEQUENCE: 4

Leu Arg Glu
1

<210> SEQ ID NO 5
<211> LENGTH: 15
<212> TYPE: PRT
<213> ORGANISM: Artificial
<220> FEATURE:
<223> OTHER INFORMATION: synthetic peptide

<400> SEQUENCE: 5

Lys Cys Gln Ala Gly Thr Phe Ala Leu Arg Gly Asp Pro Gln Gly
1               5                   10                  15

<210> SEQ ID NO 6
<211> LENGTH: 3
<212> TYPE: PRT
<213> ORGANISM: Artificial
<220> FEATURE:
<223> OTHER INFORMATION: synthetic peptide

<400> SEQUENCE: 6

Arg Gly Asp
1

<210> SEQ ID NO 7
<211> LENGTH: 8
<212> TYPE: PRT
<213> ORGANISM: Artificial
<220> FEATURE:
<223> OTHER INFORMATION: synthetic peptide

<400> SEQUENCE: 7

Asp Arg Val Tyr Ile His Pro Phe
1               5

<210> SEQ ID NO 8
<211> LENGTH: 8
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: Sar

<400> SEQUENCE: 8

Xaa Arg Val Tyr Ile His Pro Ile
1               5

<210> SEQ ID NO 9
<211> LENGTH: 10
<212> TYPE: PRT
<213> ORGANISM: Artificial
<220> FEATURE:
<223> OTHER INFORMATION: synthetic peptide

<400> SEQUENCE: 9

Asp Arg Val Tyr Ile His Pro Phe His Leu
1               5                   10

<210> SEQ ID NO 10
```

```
<211> LENGTH: 14
<212> TYPE: PRT
<213> ORGANISM: Artificial
<220> FEATURE:
<223> OTHER INFORMATION: synthetic peptide

<400> SEQUENCE: 10

Asn Gln Glu Gln Val Ser Pro Leu Thr Leu Thr Leu Leu Lys
1               5                   10

<210> SEQ ID NO 11
<211> LENGTH: 15
<212> TYPE: PRT
<213> ORGANISM: Artificial
<220> FEATURE:
<223> OTHER INFORMATION: synthetic peptide

<400> SEQUENCE: 11

Asn Gln Glu Gln Val Ser Pro Leu Thr Leu Thr Leu Leu Lys Gly
1               5                   10                  15

<210> SEQ ID NO 12
<211> LENGTH: 15
<212> TYPE: PRT
<213> ORGANISM: Artificial
<220> FEATURE:
<223> OTHER INFORMATION: synthetic peptide

<400> SEQUENCE: 12

Asn Gln Glu Ala Val Ser Pro Leu Thr Leu Thr Leu Leu Lys Gly
1               5                   10                  15

<210> SEQ ID NO 13
<211> LENGTH: 6
<212> TYPE: PRT
<213> ORGANISM: Artificial
<220> FEATURE:
<223> OTHER INFORMATION: synthetic peptide

<400> SEQUENCE: 13

Asn Gln Glu Gln Val Gly
1               5

<210> SEQ ID NO 14
<211> LENGTH: 10
<212> TYPE: PRT
<213> ORGANISM: Artificial
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION

<400> SEQUENCE: 14

Leu Gly Pro Gly Gln Ser Lys Val Ile Gly
1               5                   10
```

AUTOMATED RADIOLABELLING METHOD

This application is a filing under 35 U.S.C. 371 of international application number PCT/GB2006/003758, filed Oct. 9, 2006, which claims priority to application number 0520529.9 filed Oct. 10, 2005, in Great Britain the entire disclosure of which is hereby incorporated by reference.

FIELD OF THE INVENTION

The present invention provides an automated method for the preparation of $^{123}$I-labelled radiopharmaceutical compositions, together with disposable cassettes for use in the method. The use of an automated synthesizer apparatus in the preparation of $^{123}$I-labelled radiopharmaceuticals is also described.

BACKGROUND TO THE INVENTION

Automated methods for the preparation of radiopharmaceuticals which comprise a positron-emitting radioisotope for positron emission tomography (PET) are well-established [D. Alexoff, in "Handbook of Radiopharmaceuticals", M. J. Welch & C. S. Redvanly (Eds.), pages 283-305 Wiley (2003)].

WO 02/051447 describes an automated synthesizer apparatus of the preparation of radiopharmaceuticals, which incorporates a disposable module containing pre-metered amounts of chemical reagents. The device is said to be particularly useful for the short-lived positron-emitting radioisotopes $^{11}$C, $^{13}$N, $^{15}$O and $^{18}$F.

Efforts have also been made to investigate automated radiopharmaceutical dispensing (APD) [Solanki, Hosp. Pharmac., 7(4), 94-98 (2000)].

For $^{123}$I-labelled radiopharmaceuticals, the conventional approach is to carry out the radiopharmaceutical preparation steps manually. Luurtsema et al [App. Rad. Isotop., 55, 783-788 (2001)] have, however, reported on an automated radiolabelling method for $^{123}$I- and $^{131}$I-labelled α-methyl tyrosine (IMT). Luurtsema et al do not use a cassette approach, and report that the expected better standardisation did not materialise for $^{123}$I, and that the variation in the automated synthesis requires further optimisation. Such optimisation was said to be necessary for each new radiopharmaceutical.

Whilst automation is recognised as having the potential to reduce operator radiation dose, prior art automated processes have also been reported to be much slower than the manual counterpart, which makes them less attractive [Solanki, Hosp. Pharmac., 7(4), 94-98 (2000)]. There is therefore a need for an automated approach which is fast, more flexible, less subject to variability, and which can generate larger batch sizes in a more efficient manner.

THE PRESENT INVENTION

The present invention provides an automated method for the preparation of $^{123}$I-labelled radiopharmaceutical compositions, together with disposable cassettes for use in the method. The method is particularly suitable for use in conjunction with cassette-based "automated synthesizer" apparatus which are commercially available, but currently used primarily for the preparation of short-lived PET radiopharmaceuticals. The method is particularly useful where large numbers of unit patient doses are required on a regular basis, such as in a radiopharmacy serving either multiple hospitals or a single large hospital. This permits a single determination of radiochemical purity (RCP), and hence makes the quality control (QC) process more efficient.

Higher energy cyclotrons (30 MeV) are preferred for $^{123}$I production, which tends to mean that radioisotope manufacturing occurs at sites remote from the user site. This in turn means that, in conventional $^{123}$I-radiopharmaceutical manufacture considerable losses due to radioactive decay occur during shipment of the $^{123}$I-labelled radiopharmaceutical to the end user. The need for higher radioactivity levels at the time of manufacture of the product, means that there may be stability issues (especially when the $^{123}$I-labelled radiopharmaceutical is shipped in solution). The present invention circumvents such issues since the end user could potentially prepare the $^{123}$I-labelled radiopharmaceutical at the end user site using the automated apparatus and cassettes of the present invention.

The longer half-life of $^{123}$I (13.2 hours) compared to $^{11}$C (20.4 min) and $^{18}$F (109.6 min) and even $^{99m}$Tc (6 hours), and hence reduced time-pressure, is one possible reason why there seems to have been little interest in automating $^{123}$I radiopharmaceutical processes. Another is perhaps the reliability of prior art approaches, and whether they could satisfy the GMP (Good Manufacturing Practice) requirements of the Regulatory Authorities for commercial production.

The present invention also permits the preparation of sterile $^{123}$I-labelled radiopharmaceuticals which are less amenable to preparation via conventional aqueous solution approaches, due to eg. the need to use non-aqueous solvents or to remove undesirable non-biocompatible impurities. The invention is also permits more complex syntheses, including the preparation of $^{123}$I-labelled bifunctional intermediates in situ.

The cassettes of the present invention contain the non-radioactive chemicals necessary for a given $^{123}$I-labelled radiopharmaceutical preparation. These cassettes make the present method more flexible than prior art approaches. Use of the cassettes in the preparation of $^{123}$I-labelled radiopharmaceuticals is also described.

The present invention also provides the use of a cassette-based automated synthesizer apparatus for $^{123}$I-labelled radiopharmaceutical preparation.

DETAILED DESCRIPTION OF THE INVENTION

In a first aspect, the present invention provides an automated method for the preparation of a sterile, $^{123}$I-labelled radiopharmaceutical composition which comprises an $^{123}$I-labelled biological targeting molecule in a biocompatible carrier medium, wherein said method comprises:
  (i) provision of a single use, sterile cassette which comprises a reaction vessel and separate aliquots of the following non-radioactive Reagents (A) and (B) and optionally (C) to (G), each in sterile form:
    A. the biological targeting molecule or a precursor thereof;
    B. solvent(s) suitable for the dissolution of Reagent A and Reagents C to G if present, including at least one solvent which is a biocompatible carrier medium;
    C. an oxidising agent capable of oxidising iodide ion to an electrophilic iodinating species;
    D. a supply of $^{127}$I-iodide;
    E. a non-radioactive, bifunctional derivatising reagent capable of conjugating the biological targeting molecule;

F. a terminating reagent capable of reducing said electrophilic iodinating species to iodide ion;

G. a catalyst for nucleophilic halogenation reactions;

(ii) provision of a sterile supply of $^{123}$I-iodide in a suitable container;

(iii) radioiodination of the biological targeting molecule by steps (iv), (v) or (vi);

(iv) microprocessor-controlled transfer to said reaction vessel of Reagent A and an aliquot of $^{123}$I-iodide from (ii), optionally in the presence of Reagent C, followed by mixing therein to give the $^{123}$I-labelled biological targeting molecule, with optional use of Reagent F to stop said radioiodination reaction; or alternatively (v) radioiodination of the bifunctional derivatising reagent by microprocessor-controlled transfer to said reaction vessel of Reagent E and an aliquot of $^{123}$I-iodide from (ii), optionally in the presence of Reagent C, followed by mixing therein to give the $^{123}$I-labelled bifunctional derivatising reagent, with optional use of Reagent F to stop said radioiodination reaction, followed by radioiodination of the biological targeting molecule by conjugation with said $^{123}$I-labelled bifunctional derivatising reagent; or alternatively (vi) when Reagent A is suitable for halogen exchange reactions, microprocessor-controlled transfer to said reaction vessel of Reagent A and an aliquot of $^{123}$I-iodide from (ii), optionally in the presence of Reagent G, followed by mixing therein to give the $^{123}$I-labelled biological targeting molecule, with optional use of heating to accelerate said radioiodination reaction;

(vii) when the $^{123}$I-labelled biological targeting molecule product of steps (iv) to (vi) is already in a biocompatible carrier medium, it is used directly in step (viii), otherwise the product of steps (iv) to (vi) is either dissolved in a biocompatible carrier medium or the solvent used in steps (iv) to (vi) is removed and the residue re-dissolved in a biocompatible carrier medium;

the product from step (vii) is either used directly or is optionally subjected to the one or more of the following additional processes: purification; pH adjustment; dilution; concentration or terminal sterilisation, to give the desired $^{123}$I radiopharmaceutical composition.

The "biocompatible carrier medium" is a fluid, especially a liquid, in which the $^{123}$I-labelled biological targeting molecule is suspended or dissolved, such that the composition is physiologically tolerable, ie. can be administered to the mammalian body without toxicity or undue discomfort. The biocompatible carrier medium is suitably an injectable carrier liquid such as sterile, pyrogen-free water for injection; an aqueous solution such as saline (which may advantageously be balanced so that the final product for injection is either isotonic or not hypotonic); an aqueous solution of one or more tonicity-adjusting substances (eg. salts of plasma cations with biocompatible counterions), sugars (e.g. glucose or sucrose), sugar alcohols (eg. sorbitol or mannitol), glycols (eg. glycerol), or other non-ionic polyol materials (eg. polyethyleneglycols, propylene glycols and the like). The biocompatible carrier medium may also comprise biocompatible organic solvents such as ethanol. Such organic solvents are useful to solubilise more lipophilic compounds or formulations. Preferably the biocompatible carrier medium is pyrogen-free water for injection, isotonic saline or an aqueous ethanol solution. The pH of the biocompatible carrier medium for intravenous injection is suitably in the range 4.0 to 10.5.

By the term "biological targeting molecule" is meant: 3-100 mer peptides or peptide analogues which may be linear peptides or cyclic peptides or combinations thereof; an enzyme substrate, antagonist or inhibitor; a synthetic receptor-binding compound; an oligonucleotide, or oligo-DNA or oligo-RNA fragments. The biological targeting molecule may be of synthetic or natural origin, but is preferably synthetic.

Suitable peptides for use in the present invention include:
somatostatin, octreotide and analogues,
peptides which bind to the ST receptor, where ST refers to the heat-stable toxin produced by *E. coli* and other micro-organisms;
laminin fragments eg. YIGSR, PDSGR, IKVAV, LRE and KCQAGTFALRGDPQG,
N-formyl peptides for targeting sites of leucocyte accumulation,
Platelet factor 4 (PF4) and fragments thereof,
RGD (Arg-Gly-Asp)-containing peptides, which may eg. target angiogenesis [R. Pasqualini et al., Nat Biotechnol. 1997 June; 15(6):542-6]; [E. Ruoslahti, Kidney Int. 1997 May; 51(5):1413-7].
peptide fragments of $\alpha_2$-antiplasmin, fibronectin or beta-casein, fibrinogen or thrombospondin. The amino acid sequences of $\alpha_2$-antiplasmin, fibronectin, beta-casein, fibrinogen and thrombospondin can be found in the following references: $\alpha_2$-antiplasmin precursor [M. Tone et al., J. Biochem, 102, 1033, (1987)]; beta-casein [L. Hansson et al, Gene, 139, 193, (1994)]; fibronectin [A. Gutman et al, FEBS Lett., 207, 145, (1996)]; thrombospondin-1 precursor [V. Dixit et al, Proc. Natl. Acad. Sci., USA, 83, 5449, (1986)]; R. F. Doolittle, Ann. Rev. Biochem., 53, 195, (1984);
peptides which are substrates or inhibitors of angiotensin, such as: angiotensin II Asp-Arg-Val-Tyr-Ile-His-Pro-Phe (E. C. Jorgensen et al, *J. Med. Chem.*, 1979, Vol 22, 9, 1038-1044) [Sar, Ile] Angiotensin II: Sar-Arg-Val-Tyr-Ile-His-Pro-Ile (R. K. Turker et al., *Science,* 1972, 177, 1203).
Angiotensin I: Asp-Arg-Val-Tyr-Ile-His-Pro-Phe-His-Leu.

Preferably the peptides of the present invention comprise antiplasmin or angiotensin II peptides. Antiplasmin peptides comprise an amino acid sequence taken from the N-terminus of:

(i) $\alpha_2$-antiplasmin,
i.e. NH$_2$-Asn-Gln-Glu-Gln-Val-Ser-Pro-Leu-Thr-Leu-Thr-Leu-Leu-Lys-OH or variants of this in which one or more amino acids have been exchanged, added or removed such as:

NH$_2$-Asn-Gln-Glu-Gln-Val-Ser-Pro-Leu-Thr-Leu-Thr-Leu-Leu-Lys-Gly-OH,

NH$_2$-Asn-Gln-Glu-Ala-Val-Ser-Pro-Leu-Thr-Leu-Thr-Leu-Leu-Lys-Gly-OH,

NH$_2$-Asn-Gln-Glu-Gln-Val-Gly-OH;
or (ii) casein
ie. Ac-Leu-Gly-Pro-Gly-Gln-Ser-Lys-Val-Ile-Gly.

By the term "cyclic peptide" is meant a sequence of 5 to 15 amino acids in which the two terminal amino acids are bonded together by a covalent bond which may be a peptide or disulphide bond or a synthetic non-peptide bond such as a thioether, phosphodiester, disiloxane or urethane bond. By the term "amino acid" is meant an L- or D-amino acid, amino acid analogue or amino acid mimetic which may be optically pure, i.e. a single enantiomer and hence chiral, or a mixture of enantiomers. Preferably the amino acids of the present invention are optically pure. By the term "amino acid mimetic" is meant synthetic analogues of naturally occurring amino acids which are isosteres, i.e. have been designed to mimic the steric and electronic structure of the natural compound. Such isosteres are well known to those skilled in the art and include but are not limited to depsipeptides, retro-inverso peptides, thioamides, cycloalkanes or 1,5-disubstituted tetrazoles [see M. Goodman, Biopolymers, 24, 137, (1985)].

Synthetic peptides of the present invention may be obtained by conventional solid phase synthesis, as described in P. Lloyd-Williams, F. Albericio and E. Girald; *Chemical Approaches to the Synthesis of Peptides and Proteins*, CRC Press, 1997.

Suitable enzyme substrates, antagonists or inhibitors include glucose and glucose analogues such as fluorodeoxyglucose; fatty acids, or elastase, Angiotensin II or metalloproteinase inhibitors. A preferred non-peptide Angiotensin II antagonist is Losartan.

Suitable synthetic receptor-binding compounds include estradiol, estrogen, progestin, progesterone and other steroid hormones; ligands for the dopamine D-1 or D-2 receptor, or dopamine transporter such as tropanes; and ligands for the serotonin receptor.

Preferred biological targeting molecules of the present invention are dopamine transporter ligands such as tropanes; fatty acids; dopamine D-2 receptor ligands; benzamides; amphetamines; benzylguanidines, iomazenil, benzofuran (IBF) or hippuric acid. Preferred tropane derivatives are $^{123}$I-CIT (Dopascan™), $^{123}$I-CIT-FP (DaTSCAN™) and the E isomer of $^{123}$I-2β-carbomethoxy-3,β-(4-fluorophenyl)-N-(1-iodoprop-1-en-3-yl)nortropane (Altropane™). Dopascan™ and DaTSCAN™ are especially preferred. These and other tropane agents are described by Morgan and Nowotnik [Drug News Perspect., 12(3), 137-145 (1999). Preferred fatty acids are $^{123}$I-BMIPP and $^{123}$I-IPPA. Preferred amphetamine derivatives are $^{123}$I-IMP. A preferred benzylguanidine is meta-iodobenzylguanidine (MIBG), ie. $^{123}$I-MIBG.

The "precursor" comprises a non-radioactive derivative of the biological targeting molecule, designed so that chemical reaction with a convenient chemical form of $^{123}$I radioisotope (especially $^{123}$I-iodide) occurs site-specifically; can be conducted in the minimum number of steps (ideally a single step); and without the need for significant purification (ideally no further purification), to give the desired radioactive product. Such precursors are synthetic and can conveniently be obtained in good chemical purity. The "precursor" may optionally comprise a protecting group (P$^{GP}$) for certain functional groups of the biological targeting molecule. Suitable precursors and their methods of preparation are described by Bolton, J. Lab. Comp. Radiopharm., 45, 485-528 (2002).

By the term "protecting group" (P$^{GP}$) is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. Protecting groups are well known to those skilled in the art and are suitably chosen from, for amine groups: Boc (where Boc is tert-butyloxycarbonyl), Fmoc (where Fmoc is fluorenylmethoxycarbonyl), trifluoroacetyl, allyloxycarbonyl, Dde [i.e. 1-(4,4-dimethyl-2,6-dioxocyclohexylidene)ethyl] or Npys (i.e. 3-nitro-2-pyridine sulfenyl); and for carboxyl groups: methyl ester, tert-butyl ester or benzyl ester. For hydroxyl groups, suitable protecting groups are: methyl, ethyl or tert-butyl; alkoxymethyl or alkoxyethyl; benzyl; acetyl; benzoyl; trityl (Trt) or trialkylsilyl such as (tert-butyl) dimethylsilyl. For thiol groups, suitable protecting groups are: trityl and 4-methoxybenzyl. The use of further protecting groups are described in 'Protective Groups in Organic Synthesis', Theorodora W. Greene and Peter G. M. Wuts, (Third Edition, John Wiley & Sons, 1999). Preferably, the precursor does not comprise a protecting group, since that will typically require an additional process step to remove the protecting group.

Preferred precursors are those which comprise a derivative which either undergoes electrophilic or nucleophilic iodination or undergoes condensation with a labelled aldehyde or ketone. Examples of the first category are:

(a) organometallic derivatives such as a trialkylstannane (eg. trimethylstannyl or tributylstannyl), or a trialkylsilane (eg. trimethylsilyl) or an organoboron compound (eg. boronate esters or organotrifluoroborates);

(b) a non-radioactive alkyl/aryl bromide or iodide for halogen exchange;

(c) alkyl/aryl tosylates, mesylates or triflates for nucleophilic iodination;

(d) aromatic rings activated towards electrophilic iodination (eg. phenols);

(e) aromatic rings activated towards nucleophilic iodination (eg. aryl iodonium salts, aryl diazonium, aryl trialkylammonium salts or nitroaryl derivatives);

(f) electron deficient aromatic rings suitable for nucleophilic iodination, such as hippurate and 2-iodobenzylguanidine.

The use of aryl iodide precursors which are not activated towards nucleophilic exchange typically requires the use of a catalyst for nucleophilic halogenation reactions, as described below.

The precursor preferably comprises: a non-radioactive halogen atom such as an aryl iodide or bromide (to permit radioiodine exchange); an activated precursor aryl ring (e.g. a phenol group); an organometallic precursor compound (eg. trialkyltin, trialkylsilyl or organoboron compound); or an organic precursor such as triazenes or a good leaving group for nucleophilic substitution such as an iodonium salt. Precursors and methods of introducing radioiodine into organic molecules are described by Bolton [J. Lab. Comp. Radiopharm., 45, 485-528 (2002)]. Precursors and methods of introducing radioiodine into proteins are described by Wilbur [Bioconj. Chem., 3(6), 433-470 (1992)]. Suitable boronate ester organoboron compounds and their preparation are described by Kabalaka et al [Nucl. Med. Biol., 29, 841-843 (2002) and 30, 369-373(2003)]. Suitable organotrifluoroborates and their preparation are described by Kabalaka et al [Nucl. Med. Biol., 31, 935-938 (2004)].

Examples of suitable precursor aryl groups to which radioactive halogens, especially iodine can be attached are given below:

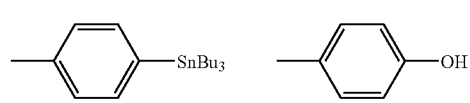

Both contain substituents which permit facile radioiodine substitution onto the aromatic ring. Alternative substituents containing radioactive iodine can be synthesised by direct iodination via radiohalogen exchange, e.g.

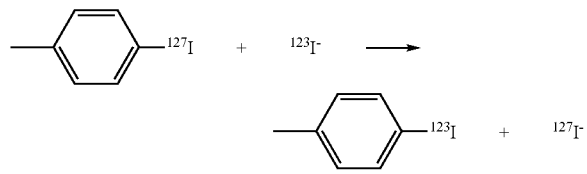

The radioiodine atom is preferably attached via a direct covalent bond to an aromatic ring such as a benzene ring, or a vinyl group since it is known that iodine atoms bound to saturated aliphatic systems are prone to in vivo metabolism and hence loss of the radioiodine.

The "precursor" may optionally be supplied covalently attached to a solid support matrix, as is described for the second embodiment below.

By the term "cassette" is meant a piece of apparatus designed to fit removably and interchangeably onto an automated synthesizer apparatus (as defined below), in such a way that mechanical movement of moving parts of the synthesizer controls the operation of the cassette from outside the cassette, ie. externally. Suitable cassettes comprise a linear array of valves, each linked to a port where reagents or vials can be attached, by either needle puncture of an inverted septum-sealed vial, or by gas-tight, marrying joints. Each valve has a male-female joint which interfaces with a corresponding moving arm of the automated synthesizer. External rotation of the arm thus controls the opening or closing of the valve when the cassette is attached to the automated synthesizer. Additional moving parts of the automated synthesizer are designed to clip onto syringe plunger tips, and thus raise or depress syringe barrels.

The cassette is versatile, typically having several positions where reagents can be attached, and several suitable for attachment of syringe vials of reagents or chromatography cartridges (eg. SPE). The cassette always comprises a reaction vessel. Such reaction vessels are preferably 1 to 10 $cm^3$, most preferably 2 to 5 $cm^3$ in volume and are configured such that 3 or more ports of the cassette are connected thereto, to permit transfer of reagents or solvents from various ports on the cassette. Preferably the cassette has 15 to 40 valves in a linear array, most preferably 20 to 30, with 25 being especially preferred. The valves of the cassette are preferably each identical, and most preferably are 3-way valves. The cassettes of the present invention are designed to be suitable for radiopharmaceutical manufacture and are therefore manufactured from materials which are of pharmaceutical grade and ideally also are resistant to radiolysis.

The term "bifunctional derivatising reagent" has its conventional meaning, ie. a non-radioactive compound having two different functional groups present: one suitable for radiolabelling with radioiodine, the other suitable for conjugation with the biological targeting molecule to give a covalent bond. The functional group suitable for radiolabelling with radioiodine suitably comprises a "precursor" group as described above. Functional groups suitable for conjugation include: amine, thiocyanate, maleimide and active esters. Such bifunctional reagents can be reacted with suitable counterpart functional groups on the biological targeting molecule to form the desired conjugate. Suitable functional groups on the biological targeting molecule include:

carboxyls (for amide bond formation with an amine-functionalised bifunctional reagent);
amines (for amide bond formation with an carboxyl- or active ester-functionalised reagent);
halogens, mesylates and tosylates (for N-alkylation of an amine-functionalised reagent) and
thiols (for reaction with a maleimide-functionalised reagents).

Amide coupling can be carried out directly (eg. using solid phase peptide synthesis), or in the presence of a suitable activating agent, such as BOP [ie. benzotriazol-1-yloxy-tris(dimethylamino)-phosphonium] or N,N'-dicyclohexylcarbodiimide (DCCI). The coupling can also be carried out via appropriate intermediates as is known in the art, such as activated esters of the carboxyl group of the biological targeting moiety. Alternatively, the pendant amine group of the bifunctional reagent can first be converted to an isothiocyanate (—NCS) or isocyanate group (—NCO) group, which permit conjugation to amine-containing biological targeting molecules, via the formation of thiourea and urea linkages respectively. Alternatively, the pendant amine group of the bifunctional reagent can be reacted with a diacid to introduce a terminal carboxyl group via a linker group. A bifunctional reagent bearing a carboxyl function can be used in a similar manner to couple directly to amine-containing biological targeting molecules via an amide bond. The bifunctional reagent may also bear a group designed to react with thiol groups on the biological targeting molecule to form stable thioether linkages. Examples of such groups are maleimides (which may be prepared by reaction of maleic anhydride with the corresponding amine, followed by heating with acetic anhydride), and acrylamides (which may be prepared by reaction of acrylyl chloride with the amine).

By the term "active ester" is meant an ester derivative of a carboxylic acid which is designed to be a better leaving group, and hence permit more facile reaction with nucleophiles present on the biological targeting moiety such as amines. Examples of suitable active esters are: N-hydroxysuccinimide (NHS), pentafluorophenol, pentafluorothiophenol, para-nitrophenol and hydroxybenzotriazole.

Suitable bifunctional derivatising agents are described by Finn ["Chemistry Applied to Iodine Radionuclides", Chapter 13 pages 423-440 in "Handbook of Radiopharmaceuticals", Welch & Redvanly (Eds), Wiley (2002)] and Wilbur [Bioconj. Chem., 3(6), 433-470 (1992)]. Preferred derivatising agents include: Bolton-Hunter [Bolton et al, Biochem. J., 133, 529-539 (1973)];
N-succinimidyl para-iodobenzoate [Zalutsky et al, App. Rad. Isot., 38, 1051-55 (1987)];
N-succinimidyl 3-OH-4-iodobenzoate [Vaidyanathan et al, Bioconj. Chem., 8, 724-9 (1997)];
N-chloro-iodotyramine [Holowaka et al, Anal. Biochem., 117, 390-7 (1981)].

By the term "oxidising agent capable of oxidising iodide ion to an electrophilic iodinating species" is meant a compound which oxidises iodide ion to iodonium ($I^+$) or similar positively charged iodine species. Preferably, the oxidising agent is chosen so that it has minimal effect on the compound to be radioiodinated, ie. Reagent A or Reagent E (the bifunctional derivatising agent). Suitable such oxidants are known in the art and include: hydrogen peroxide, Chloramine T, iodogen, peracetic acid and lactoperoxidase. Preferred such oxidants are: peracetic acid and hydrogen peroxide. It is also envisaged that the oxidation could be carried out using an electrolytic cell, which could form an additional feature of the cassette of the present invention. Such electrolytic cells have the advantage of providing controlled oxidation conditions, without the need to add chemical oxidising agents.

By the term "terminating reagent" is meant a compound which stops the radioiodination reaction, by reacting with the active radioiodination species to form a species which is no longer reactive towards the biological targeting molecule or precursor thereof. Suitable such reagents are known in the field, and include aqueous sodium metabisulphite solution. The terminating reagent may also have the function of neutralising any remaining excess oxidant, to protect $^{123}$I-labelled products which may be susceptible to oxidative degradation.

Reagent B, ie. the solvent(s) for Reagents A and B and Reagents C to G when present, could be "biocompatible carrier media" as defined above, or can be organic solvents suitable for solubilising the reagents and for carrying out the reactions of the present method. The present method thus has significant flexibility, since it is not limited to aqueous media.

By the term "catalyst for nucleophilic halogenation reactions" is meant a compound which helps accelerate such reactions, reducing reaction times and perhaps permitting the use of lower reaction temperatures. Such catalysts are known in the art, and typically include the copper ions Cu(I) or Cu(II), preferably Cu(I). [Eeersls et al, J. Lab. Comp. Radiopharm., 48(4), 241-257 (2005); Bolton, ibid, 45, 485-528 (2002) and Prabhakar et al, Appl. Rad. Isotop., 50(6), 1011-1014 (1999)]. Such catalysts are particularly useful when an unactivated precursor is to be used.

The term "microprocessor-controlled" has its conventional meaning. Thus, the term "microprocessor" as used herein, refers to a computer processor contained on an integrated circuit chip, such a processor may also include memory and associated circuits. The microprocessor is designed to perform arithmetic and logic operations using logic circuitry that responds to and processes the basic instructions that drive a computer. The microprocessor may also include programmed instructions to execute or control selected functions, computational methods, switching, etc. Microprocessors and associated devices are commercially available from a number of sources, including, but not limited to: Cypress Semiconductor Corporation, San Jose, Calif.; IBM Corporation; Applied Microsystems Corporation, Redmond, Wash., USA; Intel Corporation and National Semiconductor, Santa Clara, Calif. With regard to the present invention, the microprocessor provides a programmable series of reproducible steps involving eg. transfer of chemicals, heating, filtration etc. The microprocessor of the present invention also preferably records batch production data (eg. reagents used, reaction conditions, radioactive materials etc). This recorded data is useful to demonstrate GMP compliance for radiopharmaceutical manufacture. The microprocessor is also preferably linked to a barcode reader to permit facile selection of reaction conditions for a given production run, as described below.

The $^{123}$I radioisotope of the present invention is cyclotron-produced as is known in the art, and typically comes in the chemical form iodide in aqueous media. The $^{123}$I-iodide may optionally contain non-radioactive $^{127}$I-iodide as carrier, although it is preferred that non-radioactive $^{127}$I-iodide is included as a reagent of the cassette, as described above.

The method of the present invention may be carried out under aseptic manufacture (ie. clean room) conditions to give the desired sterile, non-pyrogenic radiopharmaceutical product. It is preferred, however, that the key components, especially the cassette and associated reagents plus those parts of the apparatus which come into contact with the radiopharmaceutical (eg. vials and transfer tubing) are sterile. The components and reagents can be sterilised by methods known in the art, including: sterile filtration, terminal sterilisation using e.g. gamma-irradiation, autoclaving, dry heat or chemical treatment (e.g. with ethylene oxide). It is preferred to sterilise the non-radioactive components in advance, so that the minimum number of manipulations need to be carried out on the $^{123}$I radiopharmaceutical. As a precaution, however, it is preferred to include at least a sterile filtration in step (viii) of the present automated method.

The precursor, oxidising agent, terminating reagent and other such reagents and solvents are each supplied in suitable vials or vessels which comprise a sealed container which permits maintenance of sterile integrity and/or radioactive safety, plus optionally an inert headspace gas (eg. nitrogen or argon), whilst permitting addition and withdrawal of solutions by syringe or cannula. A preferred such container is a septum-sealed vial, wherein the gas-tight closure is crimped on with an overseal (typically of aluminium). The closure is suitable for single or multiple puncturing with a hypodermic needle (e.g. a crimped-on septum seal closure) whilst maintaining sterile integrity. Such containers have the additional advantage that the closure can withstand vacuum if desired (eg. to change the headspace gas or degas solutions), and withstand pressure changes such as reductions in pressure without permitting ingress of external atmospheric gases, such as oxygen or water vapour. The reaction vessel is suitably chosen from such containers, and preferred embodiments thereof. The reaction vessel is preferably made of a biocompatible plastic (eg. PEEK).

The $^{123}$I-labelled radiopharmaceutical composition products of the method of the present invention are suitably supplied in a sealed container as described above, which may contain single or multiple patient doses. Single patient doses or "unit doses" can thus be withdrawn into clinical grade syringes at various time intervals during the viable lifetime of the preparation to suit the clinical situation. Preferred multiple dose containers comprise a single bulk vial (e.g. of 10 to 30 cm$^3$ volume) which contains sufficient radioactivity for multiple patient doses. Unit dose syringes are designed to be used with a single human patient only, and are therefore preferably disposable and suitable for human injection. The filled unit dose syringes may optionally be provided with a syringe shield to protect the operator from radioactive dose. Suitable such radiopharmaceutical syringe shields are known in the art and preferably comprise either lead or tungsten. The method of the present invention preferably further comprises sub-dispensing the $^{123}$I-labelled radiopharmaceutical composition into unit patient doses.

When step (viii) of the present invention includes a purification step, this could include one or more of the following:
(i) filtration to remove unwanted insoluble matter or particulates;
(ii) chromatography.

The chromatography may involve conventional normal phase or reverse phase methodology, ion exchange or size exclusion methods. It suitably takes the form of HPLC, SPE (Solid Phase Extraction) or 'flash' chromatography cartridges. In some instances the desired product is essentially immobilised at the top of a column matrix because of much higher affinity for the stationary phase compared to the mobile phase. The impurities can thus be eluted in a mobile phase to which they have higher affinity than the stationary phase to a suitably shielded waste container. After washing, the purified product can subsequently simply be eluted using an alternative eluent system to which the product exhibits higher affinity than the stationary phase. Any such chromatography is preferably carried out using disposable columns, so that there is no risk that subsequent preparations are contaminated with material from previous preparations. Such chromatography cartridges are commercially available from a range of suppliers, including Waters and Varian.

When step (viii) of the present invention includes a pH adjustment step, this can be carried out using a pH-adjusting agent. The term "pH-adjusting agent" means a compound or mixture of compounds useful to ensure that the pH of the reconstituted kit is within acceptable limits (approximately pH 4.0 to 10.5) for human or mammalian administration. Suitable such pH-adjusting agents include pharmaceutically acceptable buffers, such as tricine, phosphate or TRIS [ie. tris(hydroxymethyl)aminomethane], pharmaceutically acceptable acids such as acetic acid, bases and pharmaceutically acceptable bases such as sodium carbonate, sodium bicarbonate or mixtures thereof.

When step (vii) of the present invention includes solvent removal and re-dissolution steps, the solvent can be removed by various techniques:

(i) chromatography;
(ii) application of reduced pressure or vacuum;
(iii) evaporation due to heating or bubbling of gas through or over the solution;
(iv) azeotropic distillation.

The chromatography technique applies immobilisation as described above, and is a preferred method. Such solvent removal techniques are important because they permit the preparation of $^{123}$I-labelled radiopharmaceuticals by reaction in organic solvents, but the final radiopharmaceutical is still supplied in a biocompatible carrier medium.

This is particularly useful for precursors or intermediates which are either poorly soluble in aqueous media or susceptible to hydrolysis in aqueous media or perhaps both. Examples of this are: BZM (precursor to $^{123}$I-IBZM); trialkyltin precursors, especially tributyltin or trimethyltin derivatives. Hence, when the precursor is poorly soluble or susceptible to hydrolysis in aqueous media, the solvent used is preferably an organic solvent, most preferably a water-miscible organic solvent such as acetonitrile, ethanol, dimethylformamide (DMF), dimethylsulfoxide (DMSO) or acetone. Preferred such solvents are acetonitrile, ethanol, DMF and DMSO.

The purification method may also involve removal of excess non-radioactive precursor from the $^{123}$I-labelled radiopharmaceutical. This is particularly important when the precursor is also biologically active (eg. a peptide with affinity for a given receptor in vivo), since that removes any possibility of the precursor competing with the $^{123}$I-labelled radiopharmaceutical for the biological target site of interest in vivo. This purification can be achieved as follows: the crude product is loaded onto a HPLC pre-column. Polar impurities are washed to waste via a diverting valve which physically protects the main column and enhances purification. The product and lipophilic impurities are then transferred via valves to the main column. The product is chromatographically separated and collected. The corresponding UV signal is quantified so that specific activity can be subsequently calculated. The product fraction may optionally be processed via an SPE column to allow adjustment of the organic solvent content.

Suitable materials for the separation column which give highly efficient separation are known in the art and include: ion exchange resins, silica, alumina and reverse phase columns. Preferably the separation column is designed to be single-use, ie. disposable. Most preferably the separation column is an SPE column or a Flash Chromatography Cartridge (commercially available from a range of suppliers).

The method of the present invention may be carried out using laboratory robotics or an automated synthesizer. By the term "automated synthesizer" is meant an automated module based on the principle of unit operations as described by Satyamurthy et al [Clin. Positr. Imag., 2(5), 233-253 (1999)]. The term 'unit operations' means that complex processes are reduced to a series of simple operations or reactions, which can be applied to a range of materials. Such automated synthesizers are preferred for the method of the present invention, and are commercially available from a range of suppliers [Satyamurthy et al, above], including: GE Healthcare; CTI Inc; Ion Beam Applications S.A. (Chemin du Cyclotron 3, B-1348 Louvain-La-Neuve, Belgium); Raytest (Germany) and Bioscan (USA).

Commercial automated synthesizers also provide suitable containers for the liquid radioactive waste generated as a result of the radiopharmaceutical preparation. Automated synthesizers are not typically provided with radiation shielding, since they are designed to be employed in a suitably configured radioactive work cell. The radioactive work cell provides suitable radiation shielding to protect the operator from potential radiation dose, as well as ventilation to remove chemical and/or radioactive vapours. Suitable automated synthesizers of the present invention are those which comprise a disposable or single use cassette which comprises all the reagents, reaction vessels and apparatus necessary to carry out the preparation of a given batch of $^{123}$I-labelled radiopharmaceutical. Such cassettes are described in the second embodiment below. The cassette means that the automated synthesizer has the flexibility to be capable of making a variety of different $^{123}$I-labelled, or also $^{18}$F-labelled and other radioisotope-labelled radiopharmaceuticals with minimal risk of cross-contamination, by simply changing the cassette. The cassette approach has the advantages of: simplified set-up hence reduced risk of operator error; improved GMP compliance; multi-tracer capability; rapid change between production runs; pre-run automated diagnostic checking of the cassette and reagents; automated barcode cross-check of chemical reagents vs the synthesis to be carried out; reagent traceability; single-use and hence no risk of cross-contamination, tamper and abuse resistance. As noted above, the cassette approach is also versatile so overcomes the prior art problem of having to redesign a whole new automated synthesis apparatus each time a different radiopharmaceutical is to be prepared.

It is envisaged that the process of the present invention can be used to produce a batch of a given $^{123}$I-labelled radiopharmaceutical which comprises sufficient radioactivity for almost any number of unit patient doses. The only constraint on the upper limit of doses is the volume of the reaction vessel and the radioactive concentration which can be achieved (eg. without radiolysis of the $^{123}$I-labelled radiopharmaceutical). The number of unit patient doses per batch is suitably 1 to 200, preferably 3 to 100, most preferably 5 to 50. The commercial automated synthesizer apparatus includes a detector for the automated measurement of the radioactive content and concentration of the reactants and products, so the dose can be measured in that way.

The batch can then be sub-dispensed into multiple unit doses in suitable radiopharmaceutical containers (as described above) or clinical grade syringes as an additional feature of the present method, or the batch of several doses can be sub-dispensed as a separate exercise either manually or using a separate automated method, such as a syringe-filling apparatus. In a preferred aspect, this sub-dispensing is carried out as part of the same automated process. Most preferably, the sub-dispensing is into radiopharmaceutical containers. The capability to produce multiple doses in this manner means that the present method is particularly useful in a radiopharmacy serving a patient population wherein many separate patient doses of the same $^{123}$I-labelled radiopharmaceutical are needed on the same day.

Reagents A or E, the $^{123}$I-iodide (ii), and/or the $^{123}$I-labelled radiopharmaceutical compositions of the present invention may optionally further comprise additional components such as a radioprotectant, antimicrobial preservative, pH-adjusting agent or filler. By the term "radioprotectant" is meant a compound which inhibits degradation reactions, such as redox processes, by trapping highly-reactive free radicals, such as oxygen-containing free radicals arising from the radiolysis of water. The radioprotectants of the present invention are suitably chosen from: ascorbic acid, para-aminobenzoic acid (ie. 4-aminobenzoic acid), gentisic acid (ie. 2,5-dihydroxybenzoic acid) and salts thereof with a biocompatible cation as described above.

By the term "antimicrobial preservative" is meant an agent which inhibits the growth of potentially harmful micro-organisms such as bacteria, yeasts or moulds. The antimicrobial preservative may also exhibit some bactericidal properties, depending on the dose. The main role of the antimicrobial preservative(s) of the present invention is to inhibit the growth of any such micro-organism in the radiopharmaceutical composition post-reconstitution, ie. in the radioactive diagnostic product itself. The antimicrobial preservative may, however, also optionally be used to inhibit the growth of potentially harmful micro-organisms in one or more components of the non-radioactive kit of the present invention prior to reconstitution. Suitable antimicrobial preservative(s) include: the parabens, ie. methyl, ethyl, propyl or butyl paraben or mixtures thereof; benzyl alcohol; phenol; cresol; cetrimide and thiomersal. Preferred antimicrobial preservative(s) are the parabens.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

In a second aspect, the present invention provides a single use, sterile cassette suitable for use in the method of the first embodiment, which comprises the reaction vessel and means for carrying out the transfer and mixing of steps (iv) to (vi) and manipulations of step (vii), plus means for carrying out the optional additional process(es) of step (viii) of the method of the first embodiment. The cassette components and reagents (A)-(G) and preferred aspects thereof are as described in the first embodiment, and are in sterile, apyrogenic form.

The cassette components and reagents (A)-(G) may be sterilised by the sterilisation methods described above. One preferred method is to prepare the cassette apparatus complete with reagents (A)-(G), and carry out terminal sterilisation by either gamma irradiation or autoclaving, most preferably autoclaving. An especially preferred method is to provide each reagent in sterile form in a suitable container, as described above, and then assemble the cassette complete with reagents in a clean room environment to give the desired sterile product.

The cassette comprises the various non-radioactive chemicals and reagents necessary for the preparation of a given $^{123}$I-labelled radiopharmaceutical composition. The cassettes are designed to be disposable, but also interchangeable. This means that, having invested in a relatively expensive automated synthesizer apparatus, the user can simply then purchase the cassettes as the consumables necessary. It is envisaged that a range of cassettes each having different biological targeting molecules (or precursors thereto) therein to generate different specific $^{123}$I radiopharmaceuticals would be used in conjunction with a given automated synthesizer apparatus.

Reagent A (the biological targeting molecule or precursor as defined above) of the cassette may optionally be supplied covalently attached to a solid support matrix. In that way, the desired radiopharmaceutical product forms in solution, whereas starting materials and impurities remain bound to the solid phase. The cassette may therefore contain a cartridge which can be plugged into a suitably adapted automated synthesizer. The cartridge may contain, apart from the solid support-bound Reagent A, a column to remove unwanted iodide ion, and an appropriate vessel connected so as to allow the reaction mixture to be evaporated and allow the product to be formulated as required. The reagents and solvents and other consumables required for the automated method may also be included together with a compact disc carrying the software which allows the synthesizer to be operated in a way so as to meet the customer requirements for radioactive concentration, volumes, time of delivery etc. Conveniently, all components of the cassette are disposable to minimise the possibility of contamination between runs and will be sterile and quality assured. The facility to prepare and QC the cassette in advance of the production run is an advantage of the cassette approach, and is expected to help confer reliability and reproducibility on the preparation.

The vials and containers of reagents of the cassette may optionally be colour-coded such that it is easier for the operator to identify the materials present. This is not, however, necessary for routine production since the operator would simply use the pre-loaded cassette as supplied. The various containers of the cassette are preferably identified distinctively in a computer-readable format (eg. bar code) to permit more facile microprocessor control, quality assurance and maintenance of batch records.

In a third aspect, the present invention provides the use of an automated synthesizer apparatus which is adapted to accept the cassette of the second embodiment, for the preparation of an $^{123}$I-labelled radiopharmaceutical.

The "automated synthesizer" is as defined for the first embodiment above, such that it interfaces with the interchangeable, single use cassette of the second embodiment. This automated synthesizer is preferably used to carry out by the method of the first embodiment, including preferred embodiments thereof. Preferably, the $^{123}$I-labelled radiopharmaceutical is as defined in the first embodiment (above).

In a fourth aspect, the present invention provides the use of the cassette of the second embodiment in the preparation of a $^{123}$I-labelled radiopharmaceutical composition. Preferably, the cassette is used in the preparation method described in the first embodiment. The method and radiopharmaceutical, plus preferred embodiments thereof are as described in the first embodiment. The cassette and preferred embodiments thereof are as described in the second embodiment.

The invention is illustrated by the following non-limiting Example. Example 1 provides a prophetic description of how $^{123}$I-labelled CIT-FP could be prepared using the present invention.

EXAMPLE 1

Preparation of $^{123}$I-labelled FP-CIT (DaTSCAN™)

This is a prophetic Example.

The precursor CIT-FP and trimethyltin precursor would be prepared by the method of Baldwin et al [Nucl. Med. Biol., 22, 211-219 (1995)].

The components which would be used in DaTSCAN™ manufacture are:
1. I-123 sodium iodide in sodium hydroxide solution,
2. I-127 sodium iodide in sodium hydroxide solution,
3. 0.2M sodium acetate solution,
4. trimethyltin precursor in ethanolic solution,
5. 30% aqueous $H_2O_2$,
6. 25% aqueous $H_2SO_4$,
7. 30% aqueous $NaS_2O_5$ solution.

It is anticipated that all non-radioactive components (ie. items 2-7 above) would have acceptable shelf-life for cassette storage as reagents, and that it may be possible to co-store some components (e.g. 5, 6). The precursor (4) would, however, probably require refrigerated storage conditions, and would either be introduced into the cassette immediately before production or the whole cassette would be stored at 0-5° C. The components are predicted to be compatible with the plastic surfaces of the cassette and volumes compatible with vial and reaction vessel capacities.

The following 10 step procedure is used:
(i) $^{123}$I sodium iodide in sodium hydroxide solution is diluted with $^{127}$I sodium iodide in sodium hydroxide solution;
(ii) 0.2M sodium acetate solution is added;
(iii) the solution from (ii) would be added to the trimethyltin precursor in ethanolic solution;
(iv) 30% aqueous $H_2O_2$ and 25% aqueous $H_2SO_4$ solution are then added to commence the radioiodination, and the reaction carried out in the cassette reaction vessel for 10 mins at ambient temperature, with a reaction volume of 0.7-1.3 cm$^3$;
(v) radioiodination is then stopped using the terminating reagent 30% aqueous $NaS_2O_5$ solution;
(vi) the product is then purified by RP-HPLC with ethanol/aqueous sodium acetate as eluent;
(vii) the $^{123}$I-FP-CIT product is loaded onto an SPE column, and the column washed with water and 0.05 M NaOH, before elution of the product with ethanol as eluent.

What is claimed is:

1. An automated method for the preparation of a sterile $^{123}$I-labelled radiopharmaceutical composition which comprises an $^{123}$I-labelled biological targeting molecule in a biocompatible carrier medium, wherein said method comprises:
   (i) providing an automated synthesizer apparatus having a single use, sterile cassette which comprises a reaction vessel and separate aliquots of the following non-radioactive Reagents (A) and (B), each in sterile form:

Reagent A: the biological targeting molecule selected from the group consisting of CIT (2-carbomethoxy-3-(4-iodophenyl)tropane), CIT-FP (N-3-fluoropropyl-2-carbomethoxy-3-(4-iodophenyl)nortropane), IBZM (N-{[(2S)-1-ethylpyrrolidin-2-yl]methyl}-2-hydroxy-3-iodo-6-methoxybenzamide), MIBG (meta-iodobenzylguanidine), or BMIPPA (beta-methyl-iodophenyl-pentadecanoic acid), and benzofuran;
   Reagent B: one or more solvents for the dissolution of Reagent A, which is a biocompatible carrier medium selected from the group consisting of pyrogen-free water for injection, isotonic saline, and aqueous ethanol solution;
(ii) providing a sterile supply of $^{123}$I-iodide in a suitable container;
(iii) radioiodination of the biological targeting molecule by microprocessor-controlled transfer to the reaction vessel of Reagent A and an aliquot of $^{123}$I-iodide from (ii) followed by mixing therein to give the $^{123}$I-labelled biological targeting molecule; and
(iv) optionally subjecting the product of step (iii) to one or more of the following additional processes; chromatographic purification, pH adjustment, dilution, concentration, or terminal sterilisation, to give the desired $^{123}$I radiopharmaceutical composition;
wherein the automated synthesizer accepts the cassette in a removable and interchangeable manner such that moving parts of the automated synthesizer control the operation of the cassette from the outside of said cassette, and the automated synthesizer performs the processes of steps (iii) and (iv).

2. The method of claim 1 wherein the transfer of Reagent A and the $^{123}$I-iodide is in the presence of an oxidizing agent selected from hydrogen peroxide, chloramine T, iodogen, peracetic acid, and lactoperoxidase, and wherein the single use sterile cassette comprises a separate aliquot of the oxidizing agent in sterile form.

3. The method of claim 1 wherein a sodium metabisulfite terminating reagent for reducing the electrophilic iodinating species to iodide ion is used to stop the radioiodination reaction and wherein the single use sterile cassette comprises a separate aliquot of the terminating reagent in sterile form.

4. The method of claim 1, which further comprises sub-dispensing the $^{123}$I-labelled radiopharmaceutical composition into unit patient doses.

5. The method of claim 1, which further comprises providing Reagent A in sterile solution by automated reconstitution of a kit containing the lyophilized reagent.

6. The method of claim 1, which further comprises providing Reagent A bound to a solid phase support.

7. The method of claim 1, wherein the purification process step comprises HPLC for the removal of unlabeled Reagent A to give an $^{123}$I-labelled radiopharmaceutical composition free of Reagent A.

8. The method of claim 1, where an additional purification process step (v) is included, which comprises the removal of excess $^{123}$I-iodide.

9. The method of claim 1, where the automated synthesizer apparatus has a moving arm for interfacing with a male-female valve joint linked to said container provided in step (ii), which contains said sterile supply of $^{123}$I-iodide.

10. The method of claim 1, wherein said single use, sterile cassette comprises vials, transfer tubing, and reagents that are in sterile, apyrogenic form.

11. An automated method for the preparation of a sterile, $^{123}$I-labelled radiopharmaceutical composition which comprises an $^{123}$I-labelled biological targeting molecule in a biocompatible carrier medium, wherein said method comprises:
(i) providing an automated synthesizer apparatus having a single use, sterile cassette which comprises a reaction vessel and separate aliquots of the following non-radioactive Reagents A and B, each in sterile form:
Reagent A: the biological targeting molecule selected from the group consisting of CIT (2-carbomethoxy-3-(4-iodophenyl)tropane), CIT-FP (N-3-fluoropropyl-2-carbomethoxy-3-(4-iodophenyl)nortropane), IBZM (N-{[(2S)-1-ethylpyrrolidin-2-yl]methyl}-2-hydroxy-3-iodo-6-methoxybenzamide), MIBG (meta-iodobenzylguanidine), or BMIPPA (beta-methyl-iodophenyl-pentadecanoic acid), and benzofuran;
Reagent B: one or more solvents for the dissolution of Reagent A, which is a biocompatible carrier medium selected from the group consisting of pyrogen-free water for injection, isotonic saline, and aqueous ethanol solution;
(ii) providing a sterile supply of $^{123}$I-iodide in a suitable container;
(iii) microprocessor-controlled transfer to the reaction vessel of a non-radioactive, bifunctional derivatising reagent that has a functional group for radiolabeling with radioiodine, and selected from an amine, thiocyanate, maleimide, or active ester for conjugating the biological targeting molecule and an aliquot of $^{123}$I-iodide from (ii), followed by mixing therein to give the $^{123}$I-labelled bifunctional derivatising reagent, followed by radioiodination of the biological targeting molecule by conjugation with said $^{123}$I-labelled bifunctional derivatising reagent;
(iv) optionally subjecting the product of step (iii) to one or more of the following additional processes; chromatographic purification, pH adjustment, dilution, concentration, or terminal sterilisation, to give the desired $^{123}$I radiopharmaceutical composition;
wherein the automated synthesizer accepts the cassette in a removable and interchangeable manner such that moving parts of the automated synthesizer control the operation of the cassette from the outside of said cassette, and the automated synthesizer performs the processes of steps (iii) and (iv).

12. The method of claim 11 wherein step (iii) is in the presence of an oxidizing agent selected from hydrogen peroxide, chloramine T, iodogen, peracetic acid, and lactoperoxidase, and wherein the single use sterile cassette comprises a separate aliquot of the oxidizing agent.

13. The method of claim 11 wherein a sodium metabisulfite terminating reagent for reducing the electrophilic iodinating species to iodide ion is used to stop the radioiodination reaction and wherein the single use sterile cassette comprises a separate aliquot of the terminating reagent.

14. An automated method for the preparation of a sterile, $^{123}$I-labelled radiopharmaceutical composition which comprises an $^{123}$I-labelled biological targeting molecule in a biocompatible carrier medium, wherein said method comprises:
(i) providing an automated synthesizer apparatus having a single use, sterile cassette which comprises a reaction vessel and separate aliquots of the following non-radioactive Reagents A and B and optionally Reagent C, each in sterile form:
Reagent A: the biological targeting molecule selected from the group consisting of CIT (2-β-carbomethoxy-3β-(4-iodophenyl)tropane), CIT-FP (N-3-fluoropropyl-2β-carbomethoxy-3β-(4-iodophenyl)nortropane), IBZM (N-{[(2S)-1-ethylpyrrolidin-2-yl]methyl}-2-hydroxy-3-iodo-6-methoxybenzamide), MIBG (meta-iodobenzylguanidine), BMIPPA (beta-methyl-iodophenyl-pentadecanoic acid), and benzofuran;
Reagent B: one or more solvents for the dissolution of Reagent A and Reagent C, which is a biocompatible carrier medium selected from the group consisting of pyrogen-free water for injection, isotonic saline, and aqueous ethanol solution;

Reagent C: a copper ion catalyst for nucleophilic halogenation reactions;

(ii) providing a sterile supply of $^{123}$I-iodide in a suitable container;

(iii) radioiodination of the biological targeting molecule by microprocessor-controlled transfer to the reaction vessel of Reagent A and an aliquot of $^{123}$I-iodide from (ii), in the presence of Reagent C, followed by mixing therein to give the $^{123}$I-labelled biological targeting molecule, (iv) optionally subjecting the product of step (iii) to one or more of the following additional processes; chromatographic purification, pH adjustment, dilution, concentration, or terminal sterilisation, to give the desired $^{123}$I radiopharmaceutical composition;

wherein the automated synthesizer accepts the cassette in a removable and interchangeable manner such that moving parts of the automated synthesizer control the operation of the cassette from the outside of said cassette, and the automated synthesizer performs the processes of steps (iii) and (iv).

15. The method of claim 14, further comprising adding heat to accelerate the radioiodination reaction in step (iii).

* * * * *